(12) United States Patent
Labreche et al.

(10) Patent No.: US 7,167,815 B2
(45) Date of Patent: Jan. 23, 2007

(54) MEASURING THE INTENSITY OF ODORS

(75) Inventors: Saïd Labreche, Buzet sur Tarn (FR); Eric Chanie, Deyme (FR); Jean-Christophe Mifsud, Toulouse (FR)

(73) Assignee: Alpha M.O.S., Toulouse (FR)

( * ) Notice: Subject to any disclaimer, the term of this patent is extended or adjusted under 35 U.S.C. 154(b) by 0 days.

(21) Appl. No.: 11/064,447

(22) Filed: Feb. 22, 2005

(65) Prior Publication Data

US 2005/0208673 A1    Sep. 22, 2005

(30) Foreign Application Priority Data

Feb. 23, 2004    (EP)    ................... 04290478

(51) Int. Cl.
  *G06F 15/00* (2006.01)
(52) U.S. Cl. .................. 702/193; 702/22; 702/23; 702/24; 702/25; 702/27; 702/30; 702/32; 73/23.2; 73/23.34; 73/23.36
(58) Field of Classification Search ................ 702/181, 702/193, 22–25, 27, 30–32; 700/41; 73/23.2, 73/23.34, 23.36
See application file for complete search history.

(56) References Cited

U.S. PATENT DOCUMENTS

| | | | |
|---|---|---|---|
| 5,149,504 A | | 9/1992 | Tanaka |
| 5,177,994 A | * | 1/1993 | Moriizumi et al. ........ 73/23.34 |
| 5,373,452 A | * | 12/1994 | Guha ........................ 702/33 |
| 5,627,307 A | | 5/1997 | Hayashi |
| 6,006,583 A | | 12/1999 | Hayashi |
| 6,411,905 B1 | * | 6/2002 | Guoliang et al. ............. 702/23 |
| 6,496,742 B1 | * | 12/2002 | Labreche et al. ............. 700/47 |
| 6,496,813 B1 | * | 12/2002 | Labreche et al. ............. 706/20 |

(Continued)

FOREIGN PATENT DOCUMENTS

EP    1 336 844 A2    8/2003

(Continued)

OTHER PUBLICATIONS

Dowdeswell, R.M., et al, "Odour measurement using conducting polymer gas sensors and an artificial neural network decision system," Engineering Science and Education Journal, Jun. 1999, IEE, UK, vol. 8, No. 3, pp. 129-134.

(Continued)

*Primary Examiner*—Carol S. W. Tsai
*Assistant Examiner*—Phuong Huynh
(74) *Attorney, Agent, or Firm*—Weingarten, Schurgin, Gagnebin & Lebovici LLP

(57) ABSTRACT

The intensity of an odour can be quantified by determining what is the response of an odour sensing device to that odour, then transforming the response data to an odour intensity value based on transformation data relating to a set of selected reference odours. The transformation data includes organoleptic data indicating how odour intensity values assigned to the set of reference odours by a sensory panel depend upon the concentration of the reference compounds and includes data indicating how the response data of the odour sensing device when exposed to the set of reference odours depends upon the concentration of the reference compounds. The reference odours may be basic odours defining the dimensions of a multi-dimensional space in which odours can be defined.

25 Claims, 7 Drawing Sheets

U.S. PATENT DOCUMENTS

2002/0000115 A1     1/2002     Nakano et al.
2003/0172717 A1*     9/2003     Kita et al. ................. 73/23.34

FOREIGN PATENT DOCUMENTS

JP           05 099868         4/1993
JP           08 320316        12/1996

OTHER PUBLICATIONS

Persaud, K.C., et al, "Measurement of sensory quality using electronic sensing systems," Measurement & Control, Institute of Measurement and Control, London UK, vol. 29, No. 1, Feb. 1, 1996, pp. 17-20.

Jaubert, J.N., et al, "The Field of Odors: Toward a Universal Language for Odor Relationships," Perfumer and Flavorist, Allured Publishing Corporation, Carol Stream, IL, 1995, 20, 3, pp. 1-16.

Jeltema, M.A., et al., "Evaluation and Applications of Odor Profiling," Journal of Sensory Studies, vol. 1, 1986, pp. 123-136.

Noble, A.C., "Home of the Aroma Wheel" (4 pages) at http://wineserver.ucdavis.edu/Acnoble/waw.html.

Meilgaard, M., "Beer Flavor Wheel" (2 pages) at http://www.weekendbrewer.com/beerflavorwheel.htm.

Greenman, J. et al., "Study on the Organoleptic Intensity Scale for Measuring Oral Malodor," Journal of Dental Research, 83(1): 81-85, 2004.

* cited by examiner

MEASURING THE INTENSITY OF ODORS

This application claims priority to a European application No. 04 290 478.9 filed Feb. 23, 2004.

The present invention relates to the field of odour analysis and, more particularly, to a method and system for providing a quantitative measurement of the intensity of an odour.

The sensation of odour results from the interaction of volatile chemical substances with the olfactory system. Extensive research has been carried out relating to various aspects of odours: odour perception, the source of odours, correlation of odour with the concentration of a product, etc. In order to put the present invention into perspective, certain research that has been carried out relating to odours will be discussed below.

A number of studies have sought to analyse odours qualitatively, notably by investigating relationships between odours of some products and the chemical substances of which they are composed. More especially, efforts have been made to establish a system for classifying odours with regard to their organoleptic properties.

Andrew Dravnieks carried out research into the characteristic properties of odours relating to a certain number of molecules. A panel of 120–140 judges assessed the properties of the odours of the molecules in terms of certain descriptive terms chosen from a set of 146 possible semantic expressions (e.g. floral, woody, etc.). The results indicated to what extent the odour of a given compound was "floral", to what extent it was "woody", etc. See "Atlas of odor character profiles" by A. Dravnieks, ASTM Data Series 61, Philadelphia (1985), 353 pp.

Using an approach similar to that of Dravnieks, Jaubert et al arranged for the odiferous properties of 1400 molecules to be analyzed—see "The Field of Odors: Toward a Universal Language for Odor Relationships" by J N Jaubert, G. Gordon and J C Doré, in "Perfumer and Flavorist", 1995, 20, 3, pages 1–16. In these tests 650 different semantic expressions were used to describe the odours of the 1400 molecules. However it was found that 135 basic semantic expressions would cover the descriptions of all the molecules. By analysing the structures of the tested molecules, and the descriptions assigned to their respective odours, Jaubert was able to identify 42 reference odours which could be used for classifying odours.

The distribution of these 42 odours around 6 compounds constituting reference poles enabled Jaubert to establish a three-dimensional representation of odour space in which odours could be mapped. The 6 reference poles are indicated in Table 1 below:

TABLE 1

| Function pole | Molecule |
| --- | --- |
| Amine | isobutylamine |
| Citrus | citral |
| Terpenic | alpha-pinene |
| Sulphured | dimethyl sulphide |
| Pyrogenous | acetyl methyl pyrazine |
| Sweet and benzenoid | coumarin |

Other attempts have been made to define a multidimensional odour space in which different odours can be represented. For example, circular structures have been proposed by A. C. Noble and by Morten Meilgaard to represent the odours of wine and beer, respectively; a 17-dimensional odour space has been defined by M A Jeltema and E W Southwick (see J. Sens. Stud., Vol. 1, pages 123–136); etc.

The above research does not address the issue of how to determine a quantitative measurement of the intensity of an odour by using an analytical instrument. However, there are many applications where it would be useful to be able to determine a quantitative measurement of odour intensity. For example, when performing quality control on a foodstuff or a drink it may be desired to maintain a constant level for the intensity of the odour given off by the product. If a quantitative value can be assigned to the odour intensity then the constancy, or variability, of the odour can be monitored. Alternatively, it is useful to be able to measure odour intensity when assessing the suitability of packaging products for different applications: for example, when deciding how best to package ground coffee in order to preserve its aroma, or when seeking packaging material which itself gives off the least odour possible.

Another application where it is helpful to be able to measure odour intensity is the field of environmental monitoring. An environmental feature such as a factory may produce odours which constitute a nuisance. If the intensity of the odours given off by the environmental feature can be quantified, the environmental impact of that nuisance can be monitored.

Conventionally, odour intensity is evaluated using a panel of human testers. Some attempts have been made to develop devices for quantifying odour intensity: see, for example U.S. Pat. Nos. 5,627,307, 6,006,583 and 5,149,504.

U.S. Pat. No. 5,627,307 proposes to determine an index value for the intensity of an odour by determining how much the odour sample must be diluted in order for it to provoke a lower-than-threshold response in a particular odour sensing device. Although this method produces a value for odour intensity this value does not indicate how intensely human beings will perceive the odour. Indeed, U.S. Pat. No. 5,627,307 specifically seeks a measurement of odour intensity which is unrelated to human perception of smells.

U.S. Pat. No. 6,006,583 proposes a similar method to U.S. Pat. No. 5,627,129, but in U.S. Pat. No. 6,006,583 the threshold used by the odour sensing device corresponds to a dilution level at which human beings cease to be able to perceive the odour. However, there is no guidance as to how the method should be adapted if it is to be applied for measurement of the intensity of odours of different types.

U.S. Pat. No. 5,149,504 proposes a system for measuring the odour intensity of the exhaust fumes of an internal combustion engine. In U.S. Pat. No. 5,149,504, the exhaust fumes are put into aqueous solution and the pH of this solution is measured. The measured pH value is then used to determine an odour intensity value based on a graph relating pH value to odour intensity as perceived by humans. U.S. Pat. No. 5,149,504 also discusses earlier work in which the odour intensity of exhaust fumes were measured by measuring the concentration of formaldehyde in those fumes, based on a finding that there was a correlation between the odour intensity rating given by human testers and the concentration of formaldehyde in the exhaust fumes.

Although the measurement techniques mentioned in U.S. Pat. No. 5,194,504 provide quantitative measurements which relate to odour intensity as perceived by human beings, they are limited to the specific application that is being considered, namely, the measurement of the odour intensity of exhaust fumes from an internal combustion engine. These techniques are not generally applicable to other types of odour.

The present invention seeks to provide a method and system for providing a quantitative measurement of odour intensity using a tuneable (configurable) scale, in other words a measurement scale which is applicable (at least to some extent) regardless of the qualitative nature of the odour under study. This scale can be tuned depending upon final objectives and the domain of application.

The present invention makes use of the fact that there are two significant correlations. The first one is between the intensity of an odour as perceived by a human and the concentration of particular gases. The second significant correlation is between instrumental measurements produced by gas detecting devices and the concentration of the gases. This point is illustrated by consideration of FIGS. 1 and 2.

FIG. 1 is a graph summarising human olfactory system behaviour when exposed to an odour at different concentrations. The model represented between Th1 and Th2, is the one suggested by AFNOR (Association Française de Normalisation) standard NF V 09-019; Analyse sensorielle: Méthode d'estimation de la grandeur, ISBN 2-12-190863-3. This standard is about size estimation in sensorial analysis. The following model is used:

$$I = k * C^t$$

where:
- I: Odour intensity
- C: Product concentration
- k and t: two constants

FIG. 2 is a graph summarising the results of a typical test in which the same set of odours presented to a gas detecting device, for example, a Metal Oxide Sensor. This model depends upon sensor type. The relationship between sensor resistance and the concentration of deoxidizing gas can be expressed by the following equation over a certain range of gas concentration (between MTh1 and MTh2):

$$Rs = A[C]^{-\alpha}$$

where:
- Rs: electrical resistance of the sensor
- A: constant
- [C]: gas concentration
- α: Slope of Rs curve According to the above formula, the relationship of sensor resistance to gas concentration is linear on a logarithmic scale within a practical range of gas concentration. Since actual sensor resistance values vary from sensor to sensor, typical sensitivity characteristics are expressed as a ratio of sensor resistance in various concentrations of gases (Rs) over resistance in a certain concentration of a target gas (R0).

For other type of sensors such as Electrochemical Cell, Photoionization detector, etc., sensor response can be linear with respect to gas concentration.

As can be seen from FIG. 1, at very low concentrations, a human panel is insensitive to variations in the concentration of the odour. It is only when the concentration of the odour passes a threshold, Th1, that the human panel begins to detect it. However, from this threshold concentration Th1 up to a second threshold level, Th2, there is a relationship between the "odour intensity value" assigned to the sample by the human panel and the concentration of that sample. When the odour concentration exceeds the second threshold, Th2, the human panel is unable to detect any further changes.

It may be considered that the graph of FIG. 1 has three zones:

Zone Z1: an unresponsive zone. In this zone the human testers do not smell anything.

Zone Z2: a detection zone. In this zone the human testers smell the gas and can assign a numerical value thereto, this value varying with the gas concentration.

Zone Z3: a saturation zone. In this zone, the human testers can smell the samples but assign the highest possible value independently of sample concentration.

It should be noted that, in the detection zone, Z2, of FIG. 1, the relationship (F(C)=I) between the actual gas concentration, C, and the numerical value, I, assigned thereto by the human testers can be a simple linear function, or a much more complicated function. This relationship, F, is different for different types of gas. FIG. 1 illustrates the typical response obtained for a single gas compound.

Turning now to FIG. 2, it will be seen that, similarly to the human panel of testers, the response of a gas detector to gas samples at different concentrations has three zones: an unresponsive zone, MZ1, in which the sensor does not detect anything at all and has a minimum output, Min (either zero output or the minimum output of which it is capable), this unresponsive zone running from a minimal gas concentration up to a gas concentration at a first threshold level MTh1; a detection zone, MZ2, beginning at the first threshold level and running up to a gas concentration at a second threshold, MTh2, in which the sensor detects the odour and produces a varying output in response thereto; and a saturated zone, MZ3, beginning at the second threshold level, MTh2, in which the sensor's output is saturated (that is it takes the maximum possible value, Max, irrespective of the sample concentration). By suitable analysis it is possible to find a function, G(S)=C, relating the sensor response, S, to the gas concentration, C.

The first and second threshold levels of gas concentration, MTh1 and MTh2, are not necessarily the same as the threshold levels, Th1 and Th2, applicable for a human panel of testers.

It will be understood from a consideration of FIGS. 1 and 2 that, when the detection zone MZ2 of the gas sensor covers the detection zone Z2 of the human panel there is a correlation between the odour intensity value given by a human panel and the response of the gas sensor when exposed to the same gas compound. Now, the graph of FIG. 2 models the typical response of a gas sensor of the Metal Oxide Sensor type. However, similar correlations between human sensory data and instrumental response are seen when other types of gas sensing device are used, such as, mass spectrometers, IR spectrometers, gas phase chromatography devices, etc.

The present inventors have realized that a quantitative measurement of odour, which is meaningful with regard to human perception of odour, can be produced by:

a) measuring the response of one or more sensors in an odour measurement device when presented with an odour under test, and b) converting the response data into an odour intensity index according to a set of transformations based on organoleptic data relating to a plurality of selected reference compounds (notably organoleptic data produced by a panel of human testers) and on data relating to the response of the odour measurement device's sensors to the selected reference compounds.

The process of measuring and converting the sensor response data can be referred to as an "odour intensity measurement phase" (or, simply "measurement phase").

In the preferred embodiments of the invention, the transformations involved in step b) correspond to the combination of the following two sub-transformations:

c) converting the response of the sensor(s) in the odour measurement device to a gas concentration value based on a set of predetermined relationships between the response of the sensor(s) and gas concentration for the selected reference compounds, and d) converting the thus-determined gas concentration value into an odour intensity index according to a set of transformations based on organoleptic data relating to the concentration of said selected reference gas compounds.

In order to be able to perform the sub-transformation c), converting sensor response to a gas concentration value, it is necessary to pre-determine what transformation G is needed in order to convert sensor response(s), S, to gas concentration, C, for the selected reference gases corresponding to a set of odours. This requires preliminary tests to be performed by presenting samples of different odours, at known concentrations, to the odour measuring device (or to an instrument comprising sensors having a comparable response to those of the odour measuring device).

In order to be able to perform the sub-transformation d), converting gas concentration value into an odour intensity value on a scale that is meaningful with regard to human perception of odours, it is necessary to pre-determine what transformation F is needed in order to convert gas concentration, C, into an odour intensity value, I, for each of the selected reference gases. This requires preliminary tests to be performed by presenting the same samples of different gases, at known concentrations, to a panel of human testers. The latter is preferably specifically trained to perform odour quantification, for example according to the standard prescribed by AFNOR [NF V 09-006, Sensory Analysis—Methodology—Initiation and training in the detection and recognition of odours; and NF V09-019].

This preliminary testing by presenting samples to a panel of human testers and to an odour measurement device can be referred to as a "transformation-data acquisition phase" or a "training phase".

The reference compounds giving rise to the organoleptic data that is used to transform the response data generated for a particular odour under test are selected so as to correspond to certain reference odours. Advantageously, these reference odours can constitute basic odours with respect to which odours can be classified: for example, the reference compounds can correspond to some or all of the 6 reference poles, or the 42 reference odours, identified by Jaubert.

More generally, if a multi-dimensional odour space is defined, in which odours of different products can be represented, the reference compounds can correspond to odours which define different dimensions of this odour space.

In general, for a particular application it is preferred to use reference products which span only a portion of the total odour space. The appropriate portion to use in a given application can be identified by a suitably-trained sensory panel (i.e. trained according to a standard such as NF V 09-006 mentioned above) based on their judgment of which are the main odours involved in the chosen application. By focusing on only that portion of the odour space which is relevant for the application in question, the odour intensity index values produced by the system during the measurement phase will more closely correspond to the values that would have been produced by a sensory panel if presented with the same odour. Moreover, the time required to calculate any particular odour intensity index during the measurement phase will be reduced.

Often there is more than one product which corresponds to a particular reference odour. For example, the products cloves, phenol, and hydrogen sulphide all produce a reference odour corresponding to the description "aromatic, pharmaceutical and sulphurous". In general, only a single product will be used in the present invention to generate the organoleptic data relating to a particular reference odour. Thus a choice is often necessary as to which product will be used to generate a given reference odour.

There are a number of sources that can be used to determine which products give off which basic odours—for example, existing standards in this field (such as the AFNOR database regarding odour and perfume relationships), or published work by various researchers (such as Dravnieks' "atlas" of descriptive terms characterizing molecules, the work of Jaubert, etc). Preferably, according to the present invention the selection of which particular product is to be used to produce a given reference odour is not fixed but can be adapted to the particular context in which the odour intensity is being measured.

If the literature does not allow reference compounds selection then Gas-Chromatography—Olfactometry (GC-O) is useful for particular domains of application. The technique of sniffing the effluent gas as it emerges from the gas chromatograph, so called gas chromatography olfactometry, is used extensively to aid the detection of odorous compounds. GC-O is a unique analytical technique which associates the resolution power of capillary GC with the selectivity and sensitivity of the human nose. The area(s) of the chromatogram and sometimes specific peaks, which correspond to the taint can be identified using this method and the number and nature of the tainting species can often be ascertained.

The present invention provides a method of determining a quantitative measurement of odour intensity, the method comprising the odour intensity measurement phase mentioned above, comprising steps a) and b).

The present invention further provides a method of determining a quantitative measurement of odour intensity, the method comprising both the odour intensity measurement phase and the transformation-data acquisition phase mentioned above (i.e. both the "training phase" and the "measurement phase").

The transformation-data acquisition phase ("training phase") has two parts, that is, the testing by a human panel ("sensory testing") and the testing by an apparatus, and these do not need to be performed at the same time. In particular, the human testing could be performed in advance, for a wide range of reference odours (and associated products), and the resulting data defining the transformation functions F for these products can be stored in a database. When it is desired to quantify odour intensity in a particular application, the appropriate reference odours for that application are identified, and corresponding reference products, $r_i$, are selected. Provided that organoleptic data defining the functions $F_i$ for these products is already available in the database, at this stage it is only necessary to acquire data defining the transformation functions $G_i$ applicable within the test apparatus. It will be readily understood that the "apparatus testing" part of the transformation-data acquisition phase can test a sub-set of the reference products for which organoleptic data is obtained in the "sensory testing" part of the transformation-data acquisition phase.

Accordingly, the present invention still further provides a method of determining a quantitative measurement of odour intensity, the method comprising the above-mentioned odour intensity measurement phase and the "apparatus testing" part of the above-described transformation-data acquisition phase (on the assumption that organoleptic transformation data is already available).

The odour intensity measurement methods of the present invention have the advantage of being applicable to a wide variety of different odours.

In the methods of the present invention transformation data is used relating to a plurality of selected odorous substances. It is preferred if these substances correspond to "poles" (or "reference odours") identified in a scheme for classifying smells qualitatively, for example in one of the classification schemes mentioned above.

Fuzzy classification methods and trained neural networks can be used for finding the functions F and G in the training phase of the odour-intensity quantification method of the present invention.

The present invention yet further provides an odour intensity measurement apparatus comprising:

an odour measurement device comprising a set of odour detectors adapted to produce a response when exposed to odorant substances and means for converting sensor response data into an odour intensity index;

wherein the converting means of the odour measurement device is provided, in use, with transformation-data for converting the sensor response data generated on exposure of the odour detectors to a sample odour into an odour intensity index according to a set of transformations based on organoleptic data relating to a plurality of selected reference odours and on data indicative of the response of the odour measurement device's sensors to said selected reference compounds.

The converting means in the odour measurement apparatus of the present invention is preferably adapted to apply a weighted transformation to measured sensor response data obtained on exposure of the odour detectors to a test sample, the weights depending upon how the measured sensor response data compares with sensor response data obtained on exposure of said odour detectors to said selected reference products. The converting means may comprise a neural network adapted to apply this weighted transformation.

The odour measurement device used in the odour intensity measurement apparatus of the present invention may itself perform part of the transformation-data acquisition stage ("training phase"), in order to generate transformation data relating to the relationship, G, between sensor response, R, and the gas concentration, C, of said selected reference gases associated to a set odours. Alternatively, the odour measurement device may have access to pre-existing transformation data that is stored in a memory internal or external to the odour measurement device itself (including a memory accessible over a network connection). This pre-existing transformation data will have been generated using an odour measurement device of the same type as that now being used in the odour intensity measurement apparatus of the invention, with approximately the same device settings (e.g. operating temperature and pressure, flow rate, etc.).

Typically, the odour measurement device in the odour measurement apparatus of the present invention includes a memory for storing the transformation data to be used by the converting means. The odour intensity measurement device in the odour measurement apparatus of the present invention may be adapted for use in generating transformation data and for storing any such generated transformation data in the above-mentioned memory (if present).

The above and further features and advantages of the present invention will become clearer from the following description of a preferred embodiment thereof, given by way of example not limitation, illustrated by the accompanying drawings, in which.

Figure 7:
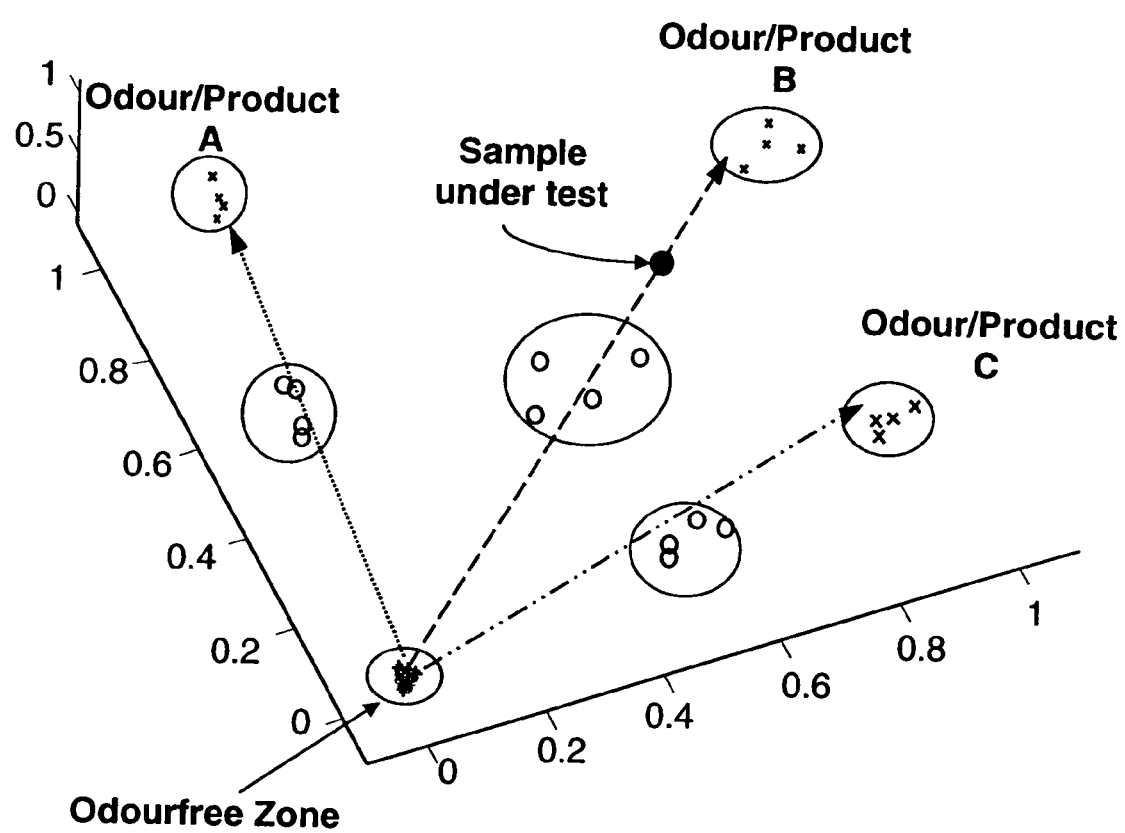
Figure 8:
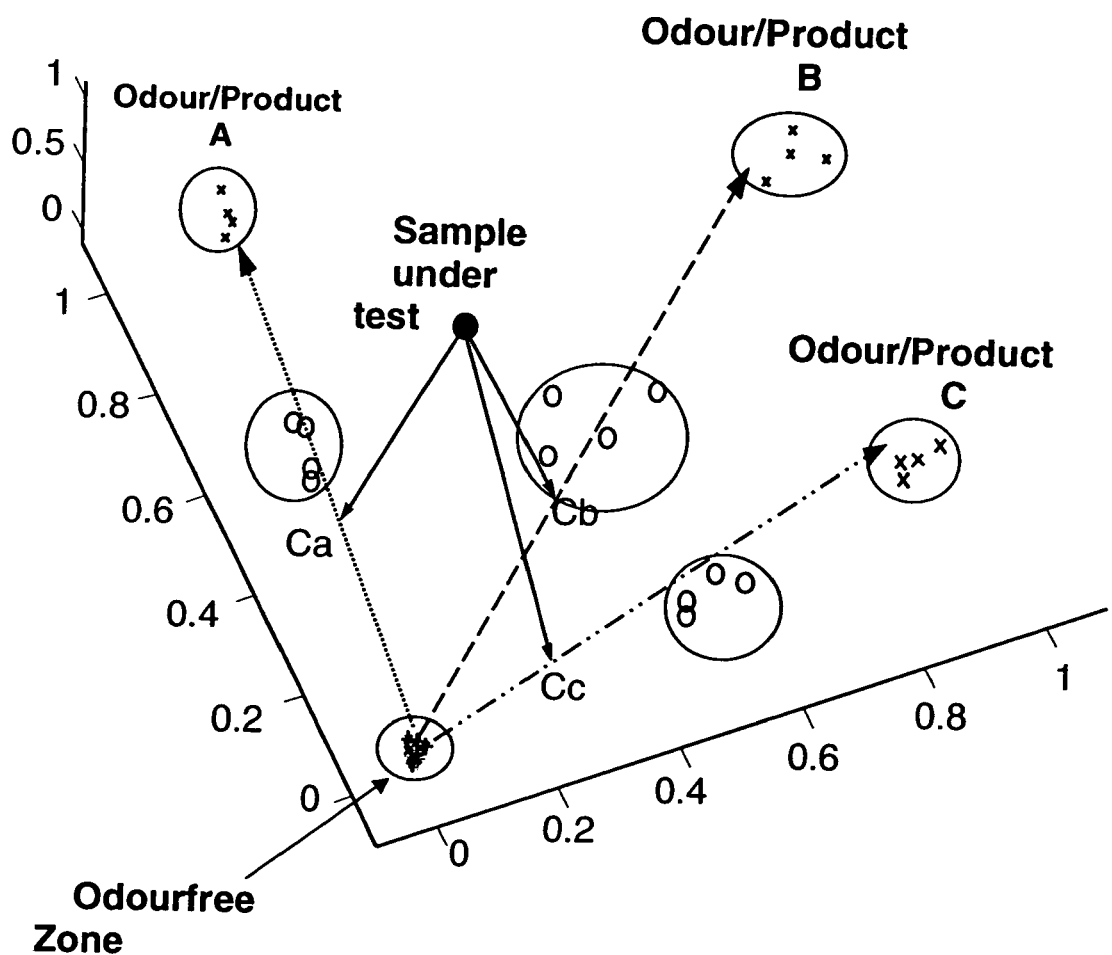

FIG. 7 is a graph illustrating the relationship between sensor response data obtained for a sample under test and sensor response data obtained for reference odours in the case where the test sample corresponds to one of the reference odours; and FIG. 8 is a graph illustrating the relationship between sensor response data obtained for a sample under test and sensor response data obtained for reference odours in the case where the test sample does not correspond to one of the reference odours.

The odour intensity quantification method of the present invention will now be described in greater detail with reference to the flow diagrams of FIGS. 3 to 6 and the graphs of FIGS. 7 and 8.

Figure 3:
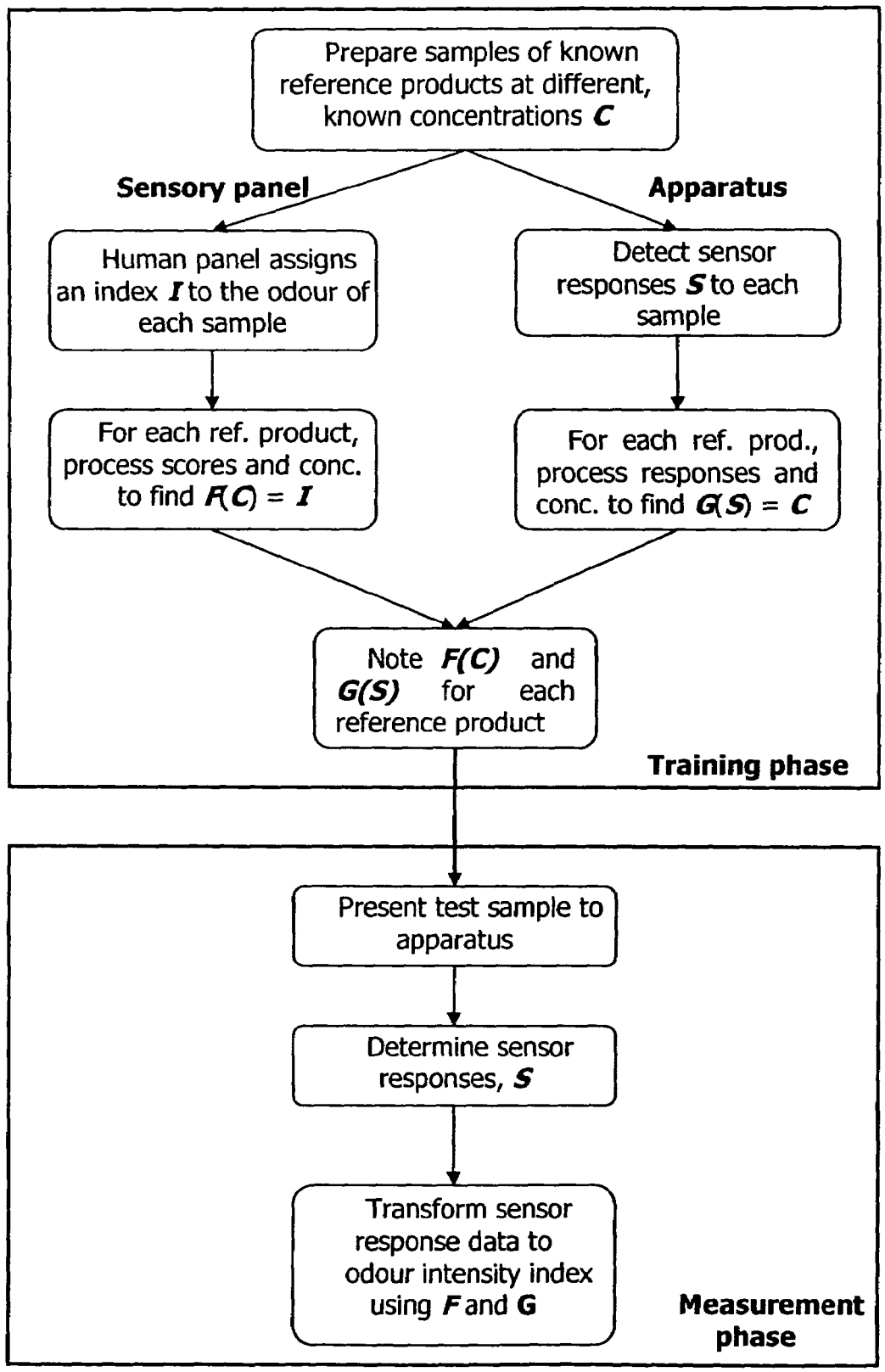
FIG. 3 is a flow diagram illustrating the main steps in one preferred embodiment of the odour intensity measurement method of the present invention.

As indicated in FIG. 3, the overall method of the preferred embodiment of the present invention has two phases: a training phase and a measurement phase.

In the training phase, samples of known reference compounds are prepared, at different, known concentrations. These samples are then presented to a sensory panel (a panel of human testers) and to a gas-sensing apparatus. For a given product, each member k of the human panel assigns an index, $I^k$, in a range running from A to B (e.g. from 1 to 10) to the odour of each sample of this product, the index indicating how intense the odour is considered to be by the human tester number k. In order to summarize the generated sensorial measures, (or "notes"), specific statistical preprocessing and methods are then applied to the individual members in the set $I^k$. The objective of this application is to substitute a global index I for the set $I^k$. Next, the odour index values are processed, together with the known concentration values, in order to determine a mathematical function, F, which relates the concentration, C, to the assigned index values, I. In other words, F is found such that F(C)=I. Data defining this function, F, is recorded in relation to this product. The procedure is repeated for each reference product. The procedure for determining F, based on C and I, is described in greater detail below.

In a similar way, when the test samples are presented to a gas-sensing apparatus, for example, an apparatus of electronic nose type containing a number of gas sensors (typically a combination of metal oxide sensors, electrochemical cells and photoionization detectors), the sensor responses are noted. For each product, a calculation is performed to see what is the function, G, which relates the sensor response data, S, to the known concentrations, C, of the test samples for that product. In other words G is found such that G(S)=C. Data defining this function, G, is recorded in relation to the associated product. This procedure is repeated for each reference product. The procedure for determining G, based on S and C, is described in greater detail below.

Thus, at the end of the training phase, data is available defining a number of functions, F, which relate the concentration of a respective reference gas compound to a perceived odour intensity index, and a number of functions, G, which relate response data of a gas sensing apparatus to the concentration of a respective reference gas compound. Preferably this data is stored so as to be available to this (or a comparable) gas sensing apparatus in a subsequent measurement phase. It is convenient if this data is stored in a non-volatile memory of the gas sensing apparatus. However, numerous alternatives are possible: for example, the data can be recorded on a CD-ROM, DVD-ROM, or other recording medium accessed via a computer system which co-operates with the gas sensing apparatus, it can be accessed via connection of the gas sensing apparatus (or an associated computer system) with a local or remote network, etc.

In the subsequent measurement phase, when it is desired to obtain a quantitative measure of the intensity of the odour of a test sample, that test sample is presented to the gas sensing apparatus. The responses of the gas sensors in the gas sensing apparatus are noted. This response data, S, is then transformed, based on the function data F and G available to the gas sensing apparatus, so as to yield an odour intensity value for the test sample.

It is possible for the training phase to generate function data, F, G, on a wide range of reference products including some which are later deemed to be irrelevant for the application in which the measurement phase will be performed. Moreover, it is possible for organoleptic function data, F, to be produced for a set of reference products which overlaps with, but is not identical to, those used to generate the "machine" function data, G. However, it is important that during the measurement phase the gas sensing apparatus has available to it organoleptic function data, F, and "machine" function data, G, for a common set of reference products.

The different stages in the method outlined above will now be described in more detail with reference to FIGS. 4 to 6.

Figure 4:
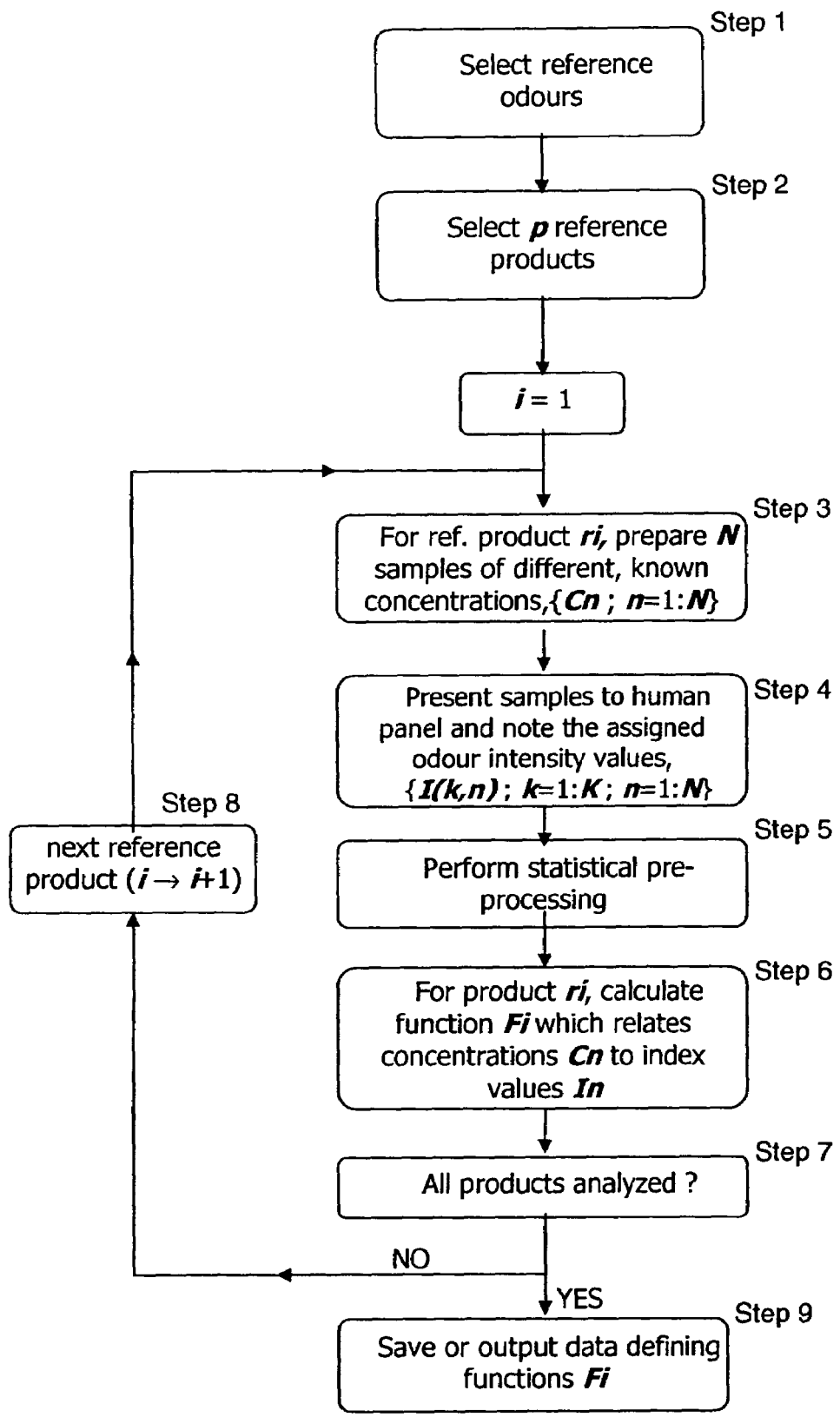
FIG. 4 is a flow diagram illustrating a process for acquiring organoleptic data F for use in transforming odour concentration data, C, to an odour intensity index, I.

FIG. 4 is a flow diagram indicating the main steps involved in the determination of the organoleptic data (notably, function, F) that relates gas compound concentration to the odour intensity index assigned by a sensory panel during the training phase.

As indicated at step 1 of FIG. 4, the first step in the process is the selection of a set of reference odours for which organoleptic data should be obtained. If the training phase is performed at a time when the final application is known, then the selection of reference odours preferably is made dependent upon that final application. For example, if the final application consists of the quantification of the intensity of the odour emitted by a waste treatment site, then the set of reference odours could comprise the following odours indicated in Table 2:

TABLE 2

| Family | Compounds | Odor |
| --- | --- | --- |
| Sulphurous | H2S, Mercaptans | Putrid, rotten egg |
| Nitrogenous | NH3, Amines | Fish, pungent |
| Aldehydes | Formaldehyde | Acrid |
| Acids | Acetic, butyric, valeric | Rancid |
| Ketones | Ketone, Methylamine | Pungent, sharp, fishy |

It is convenient to use a (suitably-trained) sensory panel to establish what are the relevant reference odours for the application in question. This is achieved by presenting typical odours to the panel and noting the semantic expressions used to describe those odours. In the case represented in Table 2, those noted semantic expressions would generally correspond to the right-hand column. Corresponding reference compounds can then be chosen, for example based on the known reference works cited above.

There is no specific limit on the number of reference odours to be used. Obviously, the duration and complexity of the training phase will increase if a large number of reference odours is used. The appropriate number will depend upon the number of principal "notes" detected by the sensory panel which is determining the reference odours to be used for the application in question. In practice, there will usually be 10 or fewer principal "notes" detected by the panel leading to the use of 10 or fewer reference odours.

If the final application is not known, or the user does not wish to have a sensory panel determine what are the reference odours, or if it is desired to have a system which is of wide applicability, then the reference odours can be selected so as to span the entirety (or a selected fraction of) odour space as defined according to any convenient classification scheme (for example, but not limited to, the scheme of Jaubert). If the odour space is defined according to Jaubert's scheme, then the whole of this odour space can be spanned if the set of reference odours corresponds to the 42 reference odours defined by Jaubert or, more efficiently, if the reference odours correspond to the 6 reference poles identified by Jaubert (that is, the reference odours correspond to the odours of isobutylamine, citral, alpha-pinene, dimethyl sulphide, acetyl methylpyrazine and coumarin—see Table 1 above).

Once the reference odours have been selected, a choice is made as to which gas compound will be used to yield each selected reference odour (step 2 of FIG. 4). As mentioned above, there can be more than one gas compound which yields a particular reference odour. Accordingly, a choice may be required as to which gas compound is going to be used in a particular case. The selected gas compounds are referred to hereafter as "reference products". In general, a single reference product will be used to generate organoleptic data relating to a particular reference odour.

Figure 1:
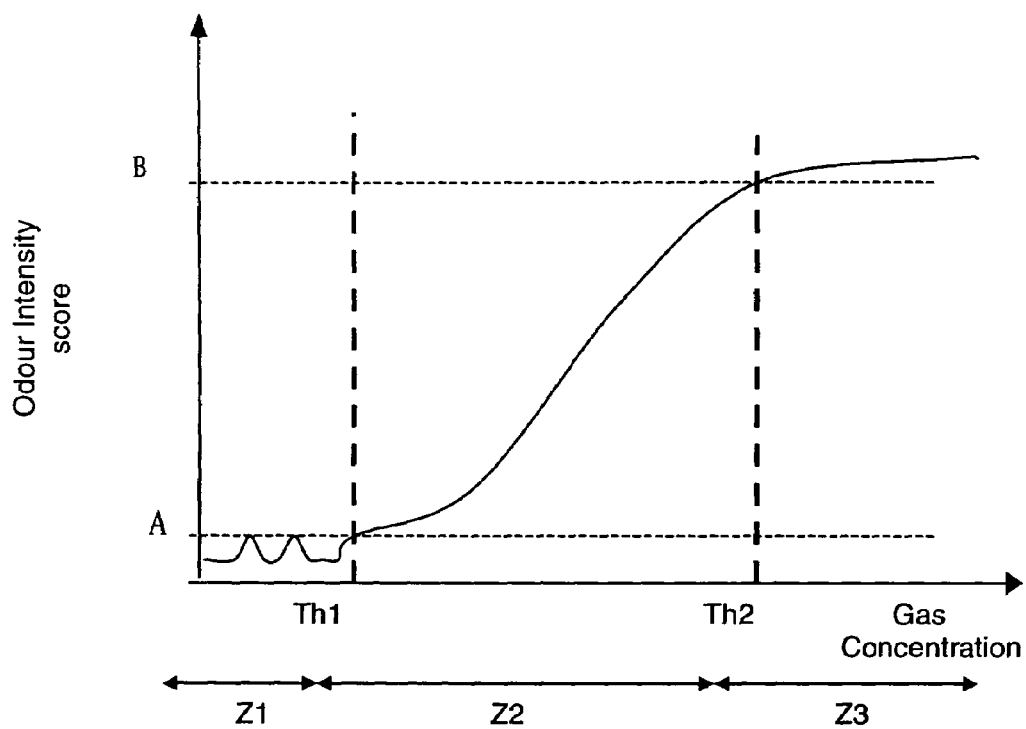
FIG. 1 is a graph illustrating how the perceived intensity of an odour varies with the concentration of the gas constituting the odour.
Figure 2:
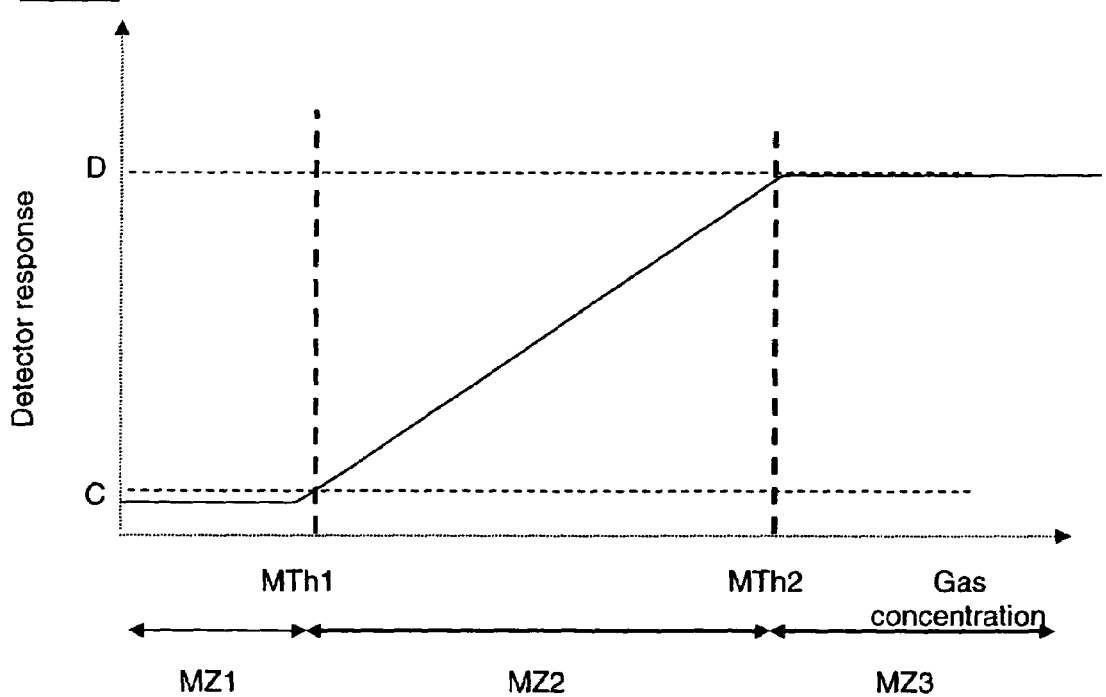
FIG. 2 is a graph illustrating how the response of a detector varies with the concentration of a gas constituting an odour.

Next, in step 3, for a first reference product, $r_i$, a number, N, of samples are prepared, each having a different (and known) concentration, $C_n$. The number of samples, and their respective concentrations, should be chosen such that they span the whole of the detection zone Z2 (see FIG. 1) and, preferably, the concentrations should be relatively evenly spaced. If there is a sharp change in the odour intensity index values that the panel assigns to two "adjacent" samples (adjacent in the direction of change of concentration) then it can be useful to prepare a new sample having a concentration intermediate between those two samples and present this new sample to the panel.

It may be the case that the threshold concentration values Th1 and Th2 are not known a priori. In such a case, a set of samples is produced with a wide range of concentration values, such that there is a good chance that this set will span the whole detection zone. Subsequently, if this is found not to be the case, extra samples may be prepared and presented to the sensory panel to estimate the different thresholds.

The test samples are presented to a panel of K human testers (step 4 of FIG. 4). Each tester k assigns a set of odour-intensity values, $\{(I(k,n); n=1:N\}$, to the samples of respective concentrations $\{C_n; n=1:N\}$ Various proposals have been made as to how a sensory panel of this type should be trained in order to produce high-quality results. Preferably the sensory panel used in the method of the present invention is one that has been trained in accordance with one of the published standards, for example the above-mentioned standards proposed by AFNOR. The odour-intensity value assigned to each sample is generally defined on a pre-arranged scale, for example a scale running from 1 to 10, with 1 indicating the mildest detectable odour and 10 indicating the most intense odour.

In order to summarize the set of generated sensorial data, specific statistical pre-processing and methods are applied to the gas concentration data, $\{C_n; n=1:N\}$ and the set of odour-intensity index data $\{I(k,n); k=1:K, n=1:N\}$ (step 5 of FIG. 4). The objectives of these steps is to transform the data set $\{I(k,n); k=1:K, n=1:N\}$ to smaller one $\{I_n; n=1:N\}$. The latter data set will contain the most (and robust) information compared with that contained in the first data set. Known methods can be used for performing this transformation, for example, one can use smoothing, means and Analysis of variance (Anova) methods, etc.

For each reference product, $r_i$, the concentration data, $C_n$, and odour-intensity index data, $I_n$, is processed (step 6 of FIG. 4) in order to find a function, $F_i$, which relates one to the other, in other words a function, $F_i$, such that:

$$F_i(C_n) = I_n$$

The function, F, may be linear or it may have a more complicated form. The function F can be found using known techniques, for example using a trained neural network, or using linear or non-linear regression techniques, etc.

Once the function F has been found, a check is made as to whether or not all of the reference products have been analyzed (step 7 of FIG. 4). If there are still unanalyzed reference products, then the index, i, of the reference product under test is increased by 1 (step 8 of FIG. 4) and steps 3 to 6 of the method are repeated for this new reference product, $r_i$. Once all of the reference products have been submitted to the sensory panel, and function data, $F_i$, obtained, this part of the method ends. The organoleptic data, that is the data defining the functions $F_i$, is saved or output in any suitable form (step 9 of FIG. 4). Typically this data will be stored as a database and recorded on any suitable recording medium. Advantageously, this organoleptic data can be programmed into a non-volatile memory of a gas sensing apparatus that is to be used to perform the measurement phase of the odour-intensity quantification method according to the present invention.

Figure 5:
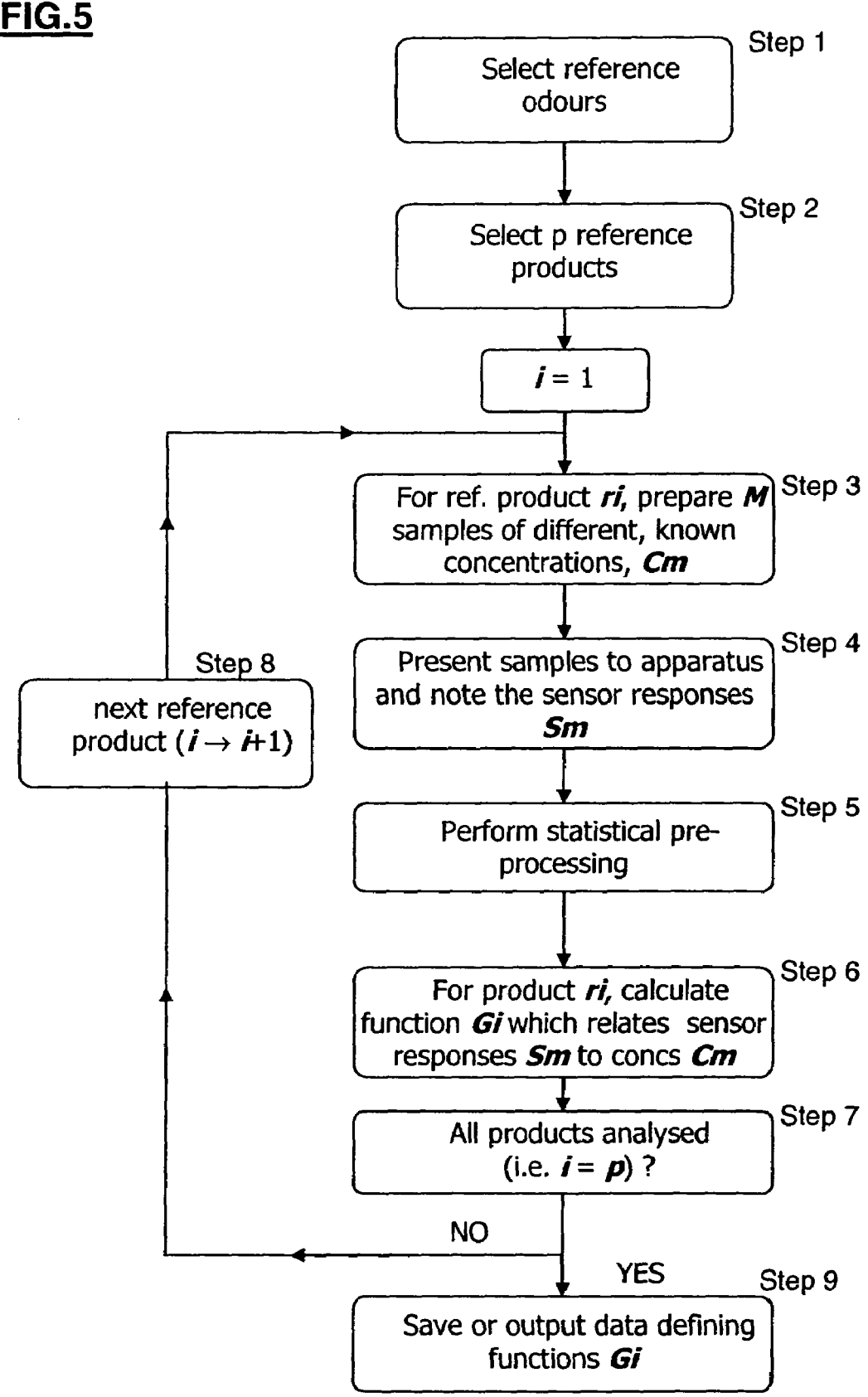
FIG. 5 is a flow diagram illustrating a process for acquiring data G for converting sensor response data, S, to odour concentration data, C.

FIG. 5 is a flow diagram indicating the main steps involved in that part of the training phase in which transformation data (notably, function, G) is determined that relates the response data, S, of sensors in a gas detecting device to the concentration, C, of a corresponding gas compound.

As indicated at steps 1 and 2 of FIG. 5, the first steps in the process are the selection of a set of reference odours for which transformation data should be obtained and the selection of a set of p reference products which yield the corresponding odours. In general, when selecting the set of reference odours and reference products for use in determining the function G, the same considerations apply as when selecting reference odours and reference products for use in determining the function, F (see the discussion above regarding steps 1 and 2 of FIG. 4).

Next, in step 3 of FIG. 5, for a reference product, $r_i$, a number, M, of samples are prepared, each having a different (and known) concentration, C. The number of samples, and their respective concentrations, should be chosen such that they span the whole of the detection zone Z2 of the sensory panel for this reference product (see FIG. 1) and, preferably, the concentrations should be relatively evenly spaced.

The test samples are presented to a gas sensing apparatus (step 4 of FIG. 5), which may be an electronic nose apparatus, mass spectrometer, IR spectrometer, gas phase chromatography device, etc. The gas sensing apparatus is adapted such that the detection zone thereof, MZ2, in respect of a particular reference product will cover the whole of the corresponding detection zone, Z2, of a human panel testing the same reference product. For example, in the case of an electronic nose device, this can be assured by a suitable choice of the number and type of sensors used within the device (e.g. by appropriate choice of sensitive layer and operating conditions used in MOS sensors or by combination of different gas sensing techniques). Sensor response data, $S_m$, is gathered for samples at respective concentrations, $C_m$.

It may be that, in respect of a particular reference product, the responses of certain sensors within the gas sensing apparatus are not particularly helpful for differentiating between gas samples at different concentrations. In such a case, it is useful to apply statistical pre-processing (step 5 of FIG. 5) so as to determine which sensor responses make a significant or appreciable contribution to differentiating between the samples at different concentrations. Preferably, only sensor data from these sensors will be used for determination of the function G. A principal components analysis or the like can be performed so as to generate composite variables, each based on the responses of one or more sensors, which can characterize the samples of different concentrations in an efficient manner.

Statistical pre-processing will also generally be applied so as to normalize the response data from the different sensors.

Next, the sensor data (which can be the data from the original set of sensors, a reduced set of the sensors, or composite variable data) is processed in order to determine a function, $G_i$, which relates the sensor response data, $S_m$, to the known concentration data, $C_m$, for each product, $r_i$ (step 6 of FIG. 5). In other words, the calculation seeks to determine $G_i$, which satisfies the relation:

$$G_i(S_m) = C_m$$

The function G is generally a linear function. If the number of sensors used in the gas detecting device is n, then the sensor response data forms a vector S having n components. The determination of G amounts to calculating n coefficients a(i) such that:

$$C_m = \sum_{j=1}^{j=n} a(j) \times S(j)$$

Various known methods can be used to determine the function G, for example a partial least squares (PLS) method can be used.

Then, a check is made as to whether or not all of the reference products have been analyzed (step 7 of FIG. 5). If there are still unanalyzed reference products, then the index, i, of the reference product under text is increased by 1 (step 8 of FIG. 5) and steps 3 to 6 of the method are repeated for this new reference product, $r_i$. Once all of the p reference products have been tested by the gas sensing apparatus, and function data, $G_i$, obtained, this part of the method ends. The transformation data, that is the data defining the functions $G_i$, is saved or output in any suitable form (step 9 of FIG. 5).

Typically this data will be stored, as a database, in a non-volatile memory of the gas sensing apparatus.

Figure 6:
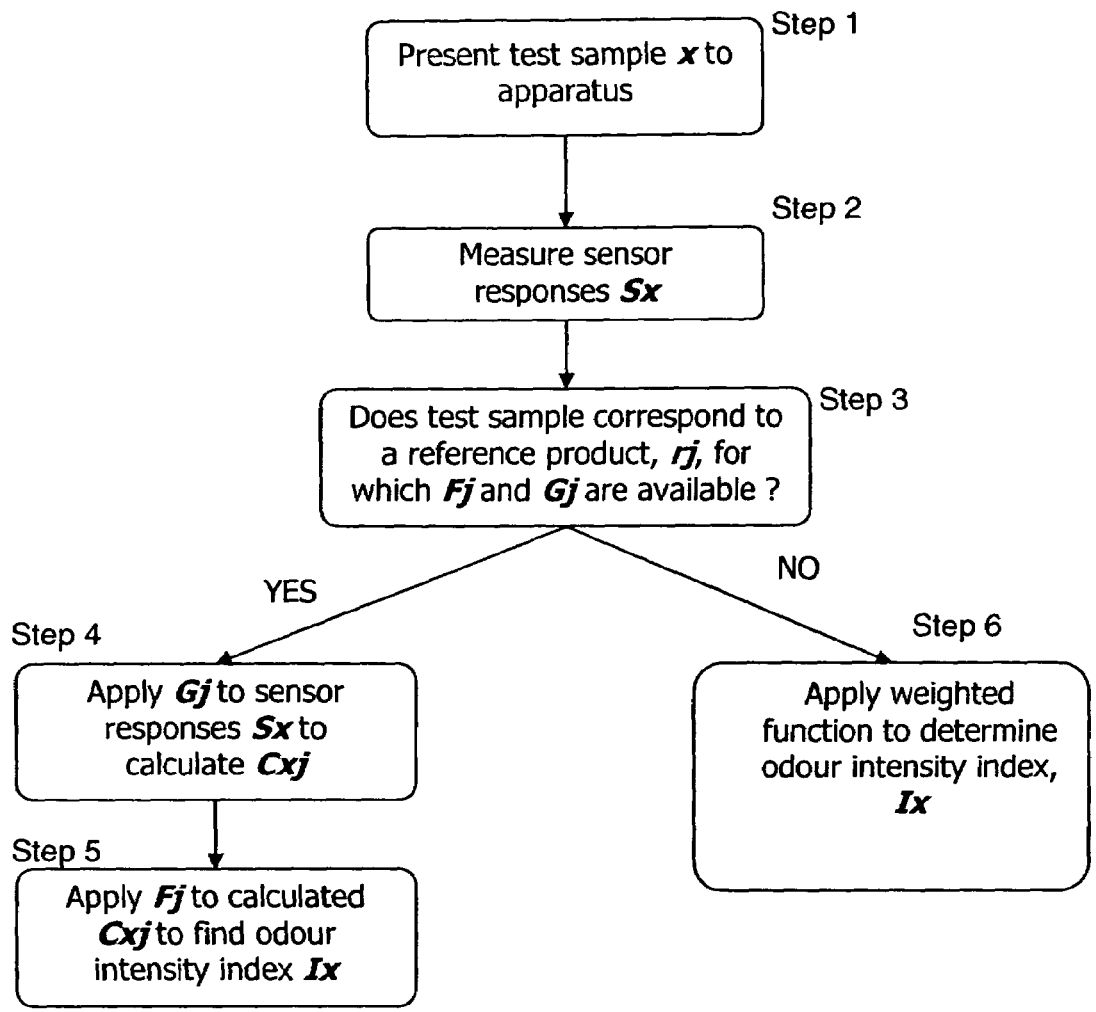
FIG. 6 is a flow diagram illustrating a process for assigning an odour intensity index value, Ix, to a sample x of a product under test.

FIG. 6 illustrates the main steps of the measurement phase of the odour-intensity quantification method according to the preferred embodiment of the present invention.

As seen in FIG. 6, in step 1 a test sample, x, is presented to a gas sensing apparatus. It is advantageous if this gas sensing apparatus is the same device as was used to generate the transformation data, $G_j$. However, the present invention also covers the case where a different device is used. The gas sensing apparatus has available to it (typically stored therein) data defining the functions F and G applicable to a set of reference odours. This set of reference odours preferably is chosen dependent upon the application in which the measurement phase is being performed.

The responses, $S_x$, of the sensors in the gas sensing apparatus to the test sample x are measured (step 2 of FIG. 6). The sensor response data, a vector Sx, is then pre-processed, for example to normalize the responses of the sensors, to determine the values of the composite variables used in a principal components analysis of the data obtained during the training phase, etc.

Next, in step 3 of FIG. 6, the sensor data representing the test sample x is compared with sensor data obtained for reference products during the training phase in order to determine whether or not the test sample corresponds to one of the reference products, $r_j$, for which function data ($F_j$, $G_j$) is available enabling this sensor data to be transformed into an odour-intensity index value. This comparison can be better understood from a consideration of FIGS. 7 and 8.

FIGS. 7 and 8 represent sensor data obtained using an electronic nose device comprising a number of MOS gas sensors. The response data generated by the MOS sensors has been subjected to a principal components analysis which yielded 3 principal components. These three principal components take normalized values between 0 and 1 and are represented using three corresponding axes in FIGS. 7 and 8.

The hollow circles and crosses shown in FIGS. 7 and 8 represent sensor data that was obtained for reference odours A, B and C (reference products A, B and C) during the training phase (which was implemented using the same electronic nose device). It will be seen that sensor data relating to the reference odour (or product) A falls along a dotted line indicated in FIGS. 7 and 8. This dotted line can be referred to as the "trajectory" of the sensor data for reference odour A. In a similar way, the sensor data that was obtained in the training phase in relation to the reference odour (product) B falls along a dashed line shown in FIGS. 7 and 8, and the sensor data that was obtained in the training phase in relation to the reference odour (product) C falls along a dot-chain line shown in FIGS. 7 and 8.

The heavy black dot in FIG. 7 indicates sensor data that was obtained when a first sample under test was submitted to the gas sensing apparatus during a measurement phase. In the case illustrated in FIG. 7 it will be seen that the heavy black dot falls on the line corresponding to data obtained for reference product B. It can therefore be assumed that the product under test has substantially the same odour as reference product B. Accordingly, when seeking to assign an odour-intensity index to this sample under test it is appropriate to use the functions F and G obtained for product B in the training phase.

Thus, for the case illustrated in FIG. 7, the result of the determination made in step 3 of FIG. 6 will be "YES", the test sample does correspond to a reference product $r_j$ for which data defining $F_j$ and $G_j$ are available. Accordingly, (step 4 of FIG. 6) the function $G_j$ can be applied to the sensor response data $S_x$ in order to obtain an estimate, $C_{xj}$, of the gas compound concentration, as follows:

$$C_{xj}=G_j(S_x)$$

It may well be the case that the sensor data, $S_x$, obtained for the sample under test, x, is close to, but not actually on, the sensory data trajectory for a particular reference odour. According to the present invention, the determination (in step 3 of FIG. 6) as to whether or not the sample under test x corresponds to a particular reference product is preferably made by considering the size of the shortest distance between the point representing the sensory data $S_x$ and the sensor-data trajectories for each of the reference products. If it is found that the distance between the test sample sensor data and a trajectory for one, $r_j$, of the reference products is less than a predetermined threshold value (which can be an absolute value, a value related to the spread of the sensory data obtained for the reference product $r_j$, etc.) then it is decided that the sample under test corresponds to $r_j$. Thus, in step 4 of FIG. 6 the function data $F_j$ and $G_j$ relating to this reference product $r_j$ will be used to transform the sensor data $S_x$ into a concentration estimate, $C_{xj}$.

In a final step (step 5 of FIG. 6), the estimate of gas compound concentration, $C_{xj}$, can then be transformed into an odour-intensity index, $I_x$, by applying $F_j$ to $C_{xj}$ as follows:

$$I_x=F_j(C_{xj})$$

It will readily be appreciated that steps 4 and 5 of FIG. 6 can be performed in a single calculation:

$$I_x=F_j(G_j(S_x))$$

Next, consideration will be given to the case where the sensor data obtained for the sample under test does not fall on (or sufficiently close to) one of the lines relating to a reference product tested during the training phase. This corresponds to the case where the result of the determination made in step 3 of FIG. 6 is "NO".

The heavy black dot in FIG. 8 indicates sensor data that was obtained when a second sample under test was submitted to the gas sensing apparatus during a measurement phase. In the case illustrated in FIG. 8 it will be seen that the heavy black dot does not fall on any of the lines corresponding to data obtained for reference products during the training phase. Accordingly, when seeking to assign an odour-intensity index to this second test sample it would not be appropriate to use function data F, G relating to a single one of the reference products.

For the case illustrated in FIG. 8, an odour-intensity index can be obtained (step 6 of FIG. 6) by applying a weighted function to the sensor data, $S_x$, obtained for the sample under test, as follows:

$$I_x = \sum_{i=1}^{p} \alpha_i F_i G_i(S_x)$$

where $\alpha_j$ are the weights assigned to the functions $F_j$, $G_j$ applicable to the jth reference odour, and $$\sum_{i=1}^{p} \alpha_i = 1.$$

The respective values of the weights, $\alpha_i$, depend upon the proximity of the sensor data for the sample under test to the lines defining the sensor data trajectories for the corresponding reference products, $r_i$. In other words, the values of the weights depend on the distance between the point defining the sensor data for the sample under test and the respective trajectories of sensor data for the p reference products. For a given reference product, $r_i$, if this distance is small then the corresponding weight $\alpha_i$ will be large. Conversely, if this distance is large then the value of the corresponding weight $\alpha_i$ will be small.

The values of these weights, $\alpha_i$, can be obtained by any one of a number of known methods: for example, using a fuzzy classification method, using a constrained neural network, using a method involving estimation of the weight or influence of each component in the analyzed odour, etc.

In the case illustrated in FIG. 8, where the sample under test does not correspond to any one of the reference products for which transformation data is available, it can be considered that the odour of the test sample can be resolved into components Ca, Cb and Cc, each indicating the extent to which the test sample sensor data corresponds to different reference odours. Thus, in this case, it is possible to determine additional odour-intensity values indicating the extent to which the test sample smells like each one of the reference products. In other words, in addition to producing an overall odour intensity index for the test sample it is possible to generate individual odour-intensity values relating to components making up the overall odour.

For example, if it is assumed that reference odour A in FIG. 8 can be designated "sulphurous", reference odour B can be designated "nitrogenous" and reference odour C can be designated "aldehydes", then the test sample represented on FIG. 8 may have an overall odour intensity of 2800 (on a scale of 1 to 100,000), with a score of 5000 for its "sulphurous" component, a score of 2500 for its "nitrogenous" component and a score of 1500 for its "aldehyde" component. This additional odour-intensity data can be useful in an application where it is desired to ensure that there is a uniform intensity not just of the overall odour of a product but also of the "constituent" odours which combine to produce that overall odour.

It will be understood that the case represented in FIG. 7, where the sample under test corresponds to one of the reference odours, is a special case of the more general situation represented in FIG. 8. More particularly, it can be considered that, when the sample under test corresponds to a particular one, $r_q$, of the reference products, then the transformation of sensor response data, $S_x$, into an odour-intensity index $I_x$ equates to the application of the weighted formula, as follows:

$$I_x = \sum_{i=1}^{p} \alpha_i F_i G_i(S_x)$$

where $\alpha_i = 1$ when $i = q$, and $\alpha_i = 0$ when $i \neq q$.

Although the present invention has been described above with reference to one preferred embodiment thereof, the person skilled in the art will readily appreciate that modifications and adaptations can be made without departing from the scope of the invention as defined in the accompanying claims.

For example, as indicated above, although it is convenient if the gas sensing apparatus used in the training phase is the same as the apparatus used in the measurement phase, this is not essential. The important factor is that the function data G obtained during the training phase should be applicable for the gas sensing apparatus used during the measurement phase (or it is known how to adapt the function data G so as to make it applicable for this apparatus).

Similarly, although the training phase can be simplified if the number and concentration of samples used to generate the organoleptic data (function F) for a given reference product is the same as the number and concentration of samples used to obtain the "machine" transformation data (function G), this is not essential. Moreover, although in the training phase it is convenient to use a single sample of a given reference product at each known concentration, it is possible to use two or more samples at each concentration.

Furthermore, although the preferred embodiments of the training phase involve separate steps of selecting reference odours and then selecting reference products which yield or correspond to these odours, it is to be understood that a single selection step, involving selection of reference products, may be involved (in other words, the reference odours are the odours of selected products).

Moreover, although the above-described preferred embodiment refers to the allocation of odour-intensity index values on a scale of 1 to 10, with 1 representing the mildest odour, other ranges of index values can be used (e.g. from 0.0 to 1.0, from 1 to 100, from 0 to 5, etc.) and the top end of the range can designate the mildest odour instead of the strongest odour.

The invention claimed is:

1. A method of measuring the intensity of an odour, the method comprising the steps of:
   providing data defining, for each of a set of reference compounds ($r_j$), a respective first function ($G_j$) indicative of the relationship between the concentration ($C_m$) of the reference compound and the response ($S_m$) of a set of odour sensors in an odour measurement device of a first type to said reference compound ($r_j$) at said concentration ($C_m$);
   providing data defining, for each of said set of reference compounds ($r_j$), a respective second function ($F_j$) indicative of the relationship between a range of different concentrations (Cn) of said reference compound and respective odour-intensity ratings ($I_n$) assigned by a sensory panel to the reference compound over said range of different concentrations (Cn);
   measuring the response ($s_x$) of a set of odour sensors in an odour measurement device of said first type when exposed to an odour sample under test (x), and
   converting the measured response data ($S_x$) into an odour intensity index ($I_x$) by applying a combination of said first and second functions to said measured response data ($S_x$).

2. An odour-intensity measurement method according to claim 1, wherein the converting step comprises the step of applying a weighted transformation to the sensor response data ($S_x$) measured in the measuring step, the weights depending upon how the measured sensor response data ($S_x$) compares with sensor response data obtained on exposure of an odour measurement device of said first type to said selected reference compounds ($r_j$).

3. An odour-intensity measurement method according to claim 2, wherein the step of applying a weighted transformation comprises the step of applying a method selected from the group consisting of: a fuzzy classification method, a method using a constrained neural network, and a method involving estimation of the influence of each of the reference compounds on the test sample odour.

4. An odour-intensity measurement method according to claim 3, and comprising the steps of:
exposing the odour measurement device to one or more of said selected reference compounds ($r_j$), and
calculating data ($G_j$) defining first function(s) indicative of the response (S) of the odour measurement device to said one or more selected reference compounds ($r_j$), said data being useable in a subsequent implementation of the converting step;
wherein the calculating step comprises applying a partial least squares computation;
storing in a memory of the odour measurement device the data (G), calculated in the calculation step, defining the first function(s) indicative of the response (S) of said odour measurement device to said one or more reference compound(s).

5. An odour-intensity measurement method according to claim 4, wherein the step of exposing the odour measurement device to one or more of the selected reference compounds ($r_j$) comprises, for each reference compound, the step of exposing the odour measurement device to a set of samples having a range of concentrations which cover the zone of sensitivity (Z2) of a sensory panel used to generate the data defining the second function (F) for the same reference compound ($r_j$).

6. An odour-intensity measurement method according to claim 4, wherein the measuring step uses an odour measurement device selected in the group consisting of: electronic nose devices, infra-red spectrometers, mass spectrometers, and gas chromatography devices; and further comprising the steps of:
for each of said selected reference compounds:
presenting to a sensory panel a plurality of samples of said reference compound ($r_i$), at different concentrations ($C_n$), and determining an odour-intensity index value ($I_n$) assigned to each sample by the sensory panel; and
determining a second function ($F_i$) indicative of the relationship between the odour-intensity values (I) assigned to samples by the sensory panel and the concentration (C) of the samples.

7. An odour-intensity measurement method according to claim 5, wherein the measuring step uses an odour measurement device selected in the group consisting of: electronic nose devices, infra-red spectrometers, mass spectrometers, and gas chromatography devices; and, further comprising the steps of:
for each of said selected reference compounds:
presenting to a sensory panel a plurality of samples of said reference compound ($r_i$), at different concentrations ($C_n$), and determining an odour-intensity index value ($I_n$) assigned to each sample by the sensory panel; and
determining a second function ($F_i$) indicative of the relationship between the odour-intensity values (I) assigned to samples by the sensory panel end the concentration (C) of the samples.

8. An odour-intensity measurement method according to claim 1, and comprising the steps of:
exposing the odour measurement device to one or more of said selected reference compounds ($r_j$), and
calculating data ($G_j$) defining first function(s) indicative of the response (S) of the odour measurement device to said one or more selected reference compounds ($r_j$), said data being useable in a subsequent implementation of the converting step.

9. An odour-intensity measurement method according to claim 8, wherein the calculating step comprises applying a partial least squares computation.

10. An odour-intensity measurement method according to claim 8, and comprising the step of storing in a memory of the odour measurement device the data (G), calculated in the calculation step, defining the first function(s) indicative of the response (S) of said odour measurement device to said one or more reference compound(s).

11. An odour-intensity measurement method according to claim 8, wherein the step of exposing the odour measurement device to one or more of the selected reference compounds ($r_j$) comprises, for each reference compound, the step of exposing the odour measurement device to a set of samples having a range of concentrations which cover the zone of sensitivity (Z2) of a sensory panel used to generate the data defining the second function (F) for the same reference compound ($r_j$).

12. An odour-intensity measurement method according to claim 1, wherein the measuring step uses an odour measurement device selected in the group consisting of: electronic nose devices, infra-red spectrometers, mass spectrometers, and gas chromatography devices.

13. An odour-intensity measurement method according to claim 1, and comprising the steps of:
for each of said selected reference compounds:
presenting to a sensory panel a plurality of samples of said reference compound ($r_i$), at different concentrations ($C_n$), and determining an odour-intensity index value ($I_n$) assigned to each sample by the sensory panel; and
determining a second function ($F_i$) indicative of the relationship between the odour-intensity values (I) assigned to samples by the sensory panel and the concentration (C) of the samples.

14. An odour-intensity measurement method according to claim 1, wherein the step of providing data defining a respective second function ($F_j$) for each of said set of reference compounds ($r_j$) consists of providing data defining a respective second function ($F_j$) for each of a set of basic compounds, said set of basic compounds defining a multi-dimensional space for classifying odours according to a universal odour-classification scheme.

15. An odour intensity measurement apparatus comprising:
an odour measurement device of a first type comprising a set of odour sensors adapted to produce a response (S) when exposed to odourant substances; and
means for converting sensor response data (S) of said odour measurement device into an odour intensity index (I);
wherein the converting means is provided, in use, with data defining, for each of a set of reference compounds ($r_j$), a respective first function ($G_i$) indicative of the relationship between the concentration ($C_m$) of the reference compound and the response ($S_m$) of a set of odour sensors in an odour measurement device of said first type to said reference compound ($r_j$) at said concentration ($C_m$), and with data defining, for each of said set of reference compounds ($r_j$), a respective second function ($F_j$) indicative of the relationship between a range of different concentrations (Cn) of said reference compound and odour-intensity ratings ($I_n$) assigned by a sensory panel to the reference compound over said range of different concentrations (Cn), and is adapted to generate said odour intensity index (I) by applying a combination of said first and second functions to said measured response data ($S_x$).

16. Odour intensity measurement apparatus according to claim 15, wherein the converting means is adapted to apply a weighted transformation to measured sensor response data ($S_x$) generated on exposure of said set of odour sensors to said sample odour (x), the weights depending upon how the measured sensor response data ($S_x$) compares with sensor response data obtained on exposure of an odour measurement device of said first type to said selected reference compounds.

17. Odour intensity measurement apparatus according to claim 16, wherein the converting means is adapted to apply said weighted transformation using a method selected in the group consisting of: a fuzzy classification method, a method using a constrained neural network, and a method involving estimation of the influence of each of the reference compounds on the sample odour.

18. Odour intensity measurement apparatus according to claim 17, and comprising calculation means for calculating at least some of said data ($G_j$) defining said first function(s) indicative of the response (S) of an odour measurement device of said first type to one or more of said selected reference compounds ($r_j$) when said odour measurement device is exposed to said reference compound(s);
 wherein the calculating means comprises means for applying a partial least squares computation;
 wherein the odour measurement device comprises a memory and is adapted to store in said memory the data (G), calculated by the calculation means, defining the first function(s) indicative of the response (S) of said odour measurement device to said reference compound(s); and
 wherein the odour measurement device comprises a set of odour sensors having, for each of said selected reference compounds, a zone of sensitivity (MZ2) which covers the corresponding zone of sensitivity (Z2) of a sensory panel used to generate the data defining said second function for said selected reference compound.

19. Odour intensity measurement apparatus according to claim 18, wherein the odour measurement device is a device selected in the group consisting of: electronic nose devices, infra-red spectrometers, mass spectrometers, and gas chromatography devices.

20. Odour intensity measurement apparatus according to claim 15, and comprising calculation means for calculating at least some of said data ($G_j$) defining said first function(s) indicative of the response (S) of an odour measurement device of said first type to one or more of said selected reference compounds ($r_j$) when said odour measurement device is exposed to said reference compound(s).

21. Odour intensity measurement apparatus according to claim 20, wherein the calculating means comprises means for applying a partial least squares computation.

22. Odour intensity measurement apparatus according to claim 20, wherein the odour measurement device comprises a memory and is adapted to store in said memory the data (G), calculated by the calculation means, defining the first function(s) indicative of the response (S) of said odour measurement device to said reference compound(s).

23. Odour intensity measurement apparatus according to claim 20, wherein the odour measurement device comprises a set of odour sensors having, for each of said selected reference compounds, a zone of sensitivity (MZ2) which covers the corresponding zone of sensitivity (Z2) of a sensory panel used to generate the data defining said second function for said selected reference compound.

24. Odour intensity measurement apparatus according to claim 15, wherein the odour measurement device is a device selected in the group consisting of: electronic nose devices, infra-red spectrometers, mass spectrometers, and gas chromatography devices.

25. Odour-intensity measurement apparatus according to claim 15, wherein the converting means is provided, in use, with data defining a respective second function ($F_j$) for each of a set of basic compounds, said set of basic compounds defining a multi-dimensional space for classifying odours according to a universal odour-classification scheme.

* * * * *

UNITED STATES PATENT AND TRADEMARK OFFICE
CERTIFICATE OF CORRECTION

PATENT NO. : 7,167,815 B2
APPLICATION NO. : 11/064447
DATED : January 23, 2007
INVENTOR(S) : Saïd Labreche et al.

Page 1 of 1

It is certified that error appears in the above-identified patent and that said Letters Patent is hereby corrected as shown below:

Title Page Item (54) "ODORS" should read --ODOURS--;

Column 1, line 1, "ODORS" should read --ODOURS--;

Column 17, claim 7, line 57, "panel end the" should read --panel and the--; and

Column 18, claim 15, line 53, "function $(G_i)$" should read --function $(G_j)$--.

Signed and Sealed this

Eleventh Day of December, 2007

JON W. DUDAS
*Director of the United States Patent and Trademark Office*

UNITED STATES PATENT AND TRADEMARK OFFICE
CERTIFICATE OF CORRECTION

PATENT NO. : 7,167,815 B2  Page 1 of 1
APPLICATION NO. : 11/064447
DATED : January 23, 2007
INVENTOR(S) : Saïd Labreche et al.

It is certified that error appears in the above-identified patent and that said Letters Patent is hereby corrected as shown below:

Title Page Item (54) "ODORS" should read --ODOURS--;

Column 1, line 1, "ODORS" should read --ODOURS--;

Column 17, claim 7, line 57, "panel end the" should read --panel and the--; and

Column 18, claim 15, line 53, "function $(G_i)$" should read --function $(G_j)$--.

Signed and Sealed this

Eighth Day of January, 2008

JON W. DUDAS
*Director of the United States Patent and Trademark Office*